(12) United States Patent
Petersen et al.

(10) Patent No.: US 8,315,684 B2
(45) Date of Patent: *Nov. 20, 2012

(54) OXIMETER AMBIENT LIGHT CANCELLATION

(75) Inventors: Ethan Petersen, Castro Valley, CA (US); William Shea, Livermore, CA (US); Bradford B. Chew, San Ramon, CA (US)

(73) Assignee: Covidien LP, Mansfield, MA (US)

( * ) Notice: Subject to any disclaimer, the term of this patent is extended or adjusted under 35 U.S.C. 154(b) by 1163 days.

This patent is subject to a terminal disclaimer.

(21) Appl. No.: 12/172,981

(22) Filed: Jul. 14, 2008

(65) Prior Publication Data

US 2009/0005662 A1    Jan. 1, 2009

Related U.S. Application Data

(60) Continuation of application No. 11/495,415, filed on Jul. 28, 2006, now Pat. No. 7,400,919, which is a division of application No. 10/787,854, filed on Feb. 25, 2004, now Pat. No. 7,190,985.

(51) Int. Cl.
*A61B 5/1455* (2006.01)
(52) U.S. Cl. ........................ 600/336; 600/322
(58) Field of Classification Search .................. 600/310, 600/322, 323, 336
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,781,195 A | 11/1988 | Martin |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,848,901 A | 7/1989 | Hood, Jr. |
| 4,863,265 A | 9/1989 | Flower et al. |
| 4,911,167 A | 3/1990 | Corenman et al. |
| 4,913,150 A | 4/1990 | Cheung et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,948,248 A | 8/1990 | Lehman |

(Continued)

FOREIGN PATENT DOCUMENTS

DE    19647877    5/1998

(Continued)

OTHER PUBLICATIONS

Leahy, Martin J., et al.; "Sensor Validation in Biomedical Applications," *IFAC Modelling and Control in Biomedical Systems*, Warwick, UK; pp. 221-226 (1997).

(Continued)

*Primary Examiner* — Eric Winakur

(57) ABSTRACT

A pulse oximeter method and apparatus which provides (1) a notch filter at a distance between a modulation frequency and a common multiple of commonly used power line frequencies (50, 60, 100 and 120) and also (2) a demodulation frequency greater than a highest pulse rate of a person and lower than any harmonic of 50, 60, 100 or 120 Hz, to filter ambient light interference, while choosing an optimum demodulation frequency that avoids interference from the notch filter or from harmonics of the line interference. Also, ambient light for any low frequency interference, such as power line interference, is measured both before and after each of the light emitter wavelengths and the average of the ambient light is then subtracted from the detected signal.

20 Claims, 3 Drawing Sheets

U.S. PATENT DOCUMENTS

| | | |
|---|---|---|
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,348,004 A | 9/1994 | Hollub |
| 5,349,952 A | 9/1994 | McCarthy et al. |
| 5,351,685 A | 10/1994 | Potratz |
| 5,355,880 A | 10/1994 | Thomas et al. |
| 5,368,026 A | 11/1994 | Swedlow et al. |
| 5,368,224 A | 11/1994 | Richardson et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,533,507 A | 7/1996 | Potratz |
| 5,553,614 A | 9/1996 | Chance |
| 5,555,882 A | 9/1996 | Richardson et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,662,106 A | 9/1997 | Swedlow et al. |
| 5,676,141 A | 10/1997 | Hollub |
| 5,680,857 A | 10/1997 | Pelikan et al. |
| 5,692,503 A | 12/1997 | Keunstner |
| 5,713,355 A | 2/1998 | Richardson et al. |
| 5,730,124 A | 3/1998 | Yamauchi |
| 5,746,697 A | 5/1998 | Swedlow et al. |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,803,910 A | 9/1998 | Potratz |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,846,190 A | 12/1998 | Woehrle |
| 5,871,442 A | 2/1999 | Madarasz et al. |
| 5,873,821 A | 2/1999 | Chance et al. |
| 5,885,213 A | 3/1999 | Richardson et al. |
| 5,919,134 A | 7/1999 | Diab |
| 5,920,263 A | 7/1999 | Huttenhoff et al. |
| 5,921,921 A | 7/1999 | Potratz et al. |
| 5,924,979 A | 7/1999 | Swedlow et al. |
| 5,954,644 A | 9/1999 | Dettling et al. |
| 5,995,855 A | 11/1999 | Kiani et al. |
| 5,995,856 A | 11/1999 | Mannheimer et al. |
| 5,995,859 A | 11/1999 | Takahashi |
| 6,011,985 A | 1/2000 | Athan et al. |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,385,471 B1 | 5/2002 | Mortz |
| 6,397,091 B2 | 5/2002 | Diab et al. |
| 6,397,092 B1 | 5/2002 | Norris et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,449,501 B1 | 9/2002 | Reuss |
| 6,461,305 B1 | 10/2002 | Schnall |
| 6,466,809 B1 | 10/2002 | Riley |
| 6,487,439 B1 | 11/2002 | Skladnev et al. |
| 6,496,711 B1 | 12/2002 | Athan et al. |
| 6,501,974 B2 | 12/2002 | Huiku |
| 6,501,975 B2 | 12/2002 | Diab et al. |
| 6,505,133 B1 | 1/2003 | Hanna et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,596,016 B1 | 7/2003 | Vreman et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,643,530 B2 | 11/2003 | Diab et al. |
| 6,654,621 B2 | 11/2003 | Palatnik et al. |
| 6,654,624 B2 | 11/2003 | Diab et al. |
| 6,658,276 B2 | 12/2003 | Pishney et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,748,253 B2 | 6/2004 | Norris et al. |
| 6,778,923 B2 | 8/2004 | Norris et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,930,608 B2 | 8/2005 | Grajales et al. |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,003,339 B2 | 2/2006 | Diab et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |

| | | |
|---|---|---|
| 7,047,054 B2 | 5/2006 | Benni |
| 7,047,056 B2 | 5/2006 | Hannula et al. |
| 7,062,307 B2 | 6/2006 | Norris et al. |
| 7,127,278 B2 | 10/2006 | Melker et al. |
| 7,162,306 B2 | 1/2007 | Caby et al. |
| 7,209,775 B2 | 4/2007 | Bae et al. |
| 7,221,971 B2 | 5/2007 | Diab et al. |
| 7,236,811 B2 | 6/2007 | Schmitt |
| 7,263,395 B2 | 8/2007 | Chan et al. |
| 7,272,426 B2 | 9/2007 | Schmid |
| 7,302,284 B2 | 11/2007 | Baker, Jr. et al. |
| 7,313,427 B2 | 12/2007 | Benni |
| 7,315,753 B2 | 1/2008 | Baker, Jr. et al. |
| 7,336,983 B2 | 2/2008 | Baker, Jr. et al. |
| 7,373,193 B2 | 5/2008 | Al-Ali et al. |
| 7,500,950 B2 | 3/2009 | Al-Ali et al. |
| 2001/0002206 A1 | 5/2001 | Diab et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0068859 A1 | 6/2002 | Knopp |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0028357 A1 | 2/2003 | Norris et al. |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0152965 A1 | 8/2004 | Diab et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0020894 A1 | 1/2005 | Norris et al. |
| 2005/0075548 A1 | 4/2005 | Al-Ali et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0143634 A1 | 6/2005 | Baker, Jr. et al. |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2007/0225582 A1 | 9/2007 | Diab et al. |
| 2008/0017800 A1 | 1/2008 | Benni |
| 2008/0033265 A1 | 2/2008 | Diab et al. |

FOREIGN PATENT DOCUMENTS

| | | |
|---|---|---|
| EP | 194105 | 5/1991 |
| EP | 1491135 | 12/2004 |
| JP | 3170866 | 7/1991 |
| JP | 3238813 | 10/1991 |
| JP | 7124138 | 5/1995 |
| JP | 7136150 | 5/1995 |
| JP | 3116255 | 12/2000 |
| JP | 22224088 | 8/2002 |
| JP | 23153881 | 5/2003 |
| JP | 23153882 | 5/2003 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 24261364 | 9/2004 |
| JP | 2004248819 | 9/2004 |
| JP | 2004290545 | 10/2004 |
| JP | 24329928 | 11/2004 |
| WO | WO9101678 | 2/1991 |
| WO | WO9309711 | 5/1993 |
| WO | WO9843071 | 10/1998 |
| WO | WO9932030 | 7/1999 |
| WO | WO0021438 | 4/2000 |
| WO | WO2005009221 | 2/2005 |

OTHER PUBLICATIONS

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

J. Huang, et al.; "Low Power Motion Tolerant Pulse Oximetry," *Abstracts*, A7, p. S103. (undated).

Hamilton, Patrick S., et al.; "Effect of Adaptive Motion-Artifact Reduction on QRS Detection," *Biomedical Instrumentation & Technology*, pp. 197-202 (undated).

Odagiri, Y.; "Pulse Wave Measuring Device," *Micromechatronics*, vol. 42, No. 3, pp. 6-11 (undated) (Article in Japanese—contains English summary of article).

Cysewska-Sobusaik, Anna; "Metrological Problems With noninvasive Transillumination of Living Tissues," *Proceedings of SPIE*, vol. 4515, pp. 15-24 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

R. Neumann, et al.; "Fourier Artifact suppression Technology Provides Reliable $SpO_2$," *Abstracts*, A11, p. S105. (undated).

$Red = RedMod - \dfrac{Dark1 + Dark2}{2}$ $IR = IRMod - \dfrac{Dark2 + Dark3}{2}$

US 8,315,684 B2

OXIMETER AMBIENT LIGHT CANCELLATION

This application is a continuation of Ser. No. 11/495,415, filed Jul. 28, 2006, now U.S. Pat. No. 7,400,919, which is a divisional of Ser. No. 10/787,854, filed Feb. 25, 2004, [which is a continuation of Ser. No. 11/495,415 filed Jul. 28, 2006] now U.S. Pat. No. 7,190,985.

BACKGROUND OF THE INVENTION

The present invention relates to oximeters, and in particular to techniques for ambient light cancellation in pulse oximeters.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

One problem with oximeter measurements is that in addition to receiving the light that was directed at the tissue, ambient light is also detected by the photodetector. Attempts can be made to block out ambient light, but some amount of ambient light will typically be detected. One particular concern is the light at the power line frequency of fluorescent or other lights, which is 60 Hz in the United States and 50 Hz in Europe and other countries.

Since a single photodetector is typically used, the light of different wavelengths, such as red and infrared, is time multiplexed. The detected signal must be demultiplexed. The demultiplexing frequency must be high enough so that it is much larger than the pulse rate. However, choosing a demultiplexing frequency is also impacted by the ambient light interference. One issue is the aliasing of harmonics of the AC power line frequency. U.S. Pat. No. 5,713,355 discusses a technique of altering the demultiplexing frequency depending upon the amount of ambient interference detected at each frequency.

U.S. Pat. No. 5,885,213 discusses subtracting a dark signal (detected ambient light) from the detected light signal. This is accomplished by leaving both the red and infrared light emitters off, in between turning them on, so that a "dark" signal supposedly composed of the ambient light present can be detected. This can then be subtracted from the desired signal. Other examples of patents dealing with the ambient light issue are U.S. Pat. No. 6,385,471, U.S. Pat. No. 5,846,190 and U.S. Pat. No. 4,781,195.

U.S. Pat. No. 6,449,501 discusses using a notch filter to filter out line frequency. However, the sampling rate is described as being set to twice the fundamental frequency of the power line interference, leaving higher harmonics of the power line interference as a problem, and it is unclear how the interference can be filtered without filtering the modulation frequency. Another example of a notch filter being used is set forth in U.S. Pat. No. 4,802,486, which uses a notch filter for the EKG signal.

BRIEF SUMMARY OF THE INVENTION

The present invention provides a pulse oximeter method and apparatus which provides (1) a notch filter at a distance between a demodulation frequency and a common multiple of commonly used power line frequencies (50, 60, 100, and 120) and also (2) a demodulation frequency greater than a highest pulse rate of a person and lower than any harmonic of 50, 60, 100, or 120 Hz. The invention thus allows the filtering of a significant source of ambient light interference, while choosing an optimum demodulation frequency that avoids interference from the notch filter or from harmonics of the power line interference.

In one embodiment, the common multiple is 1200, with the demodulation frequency being between 5 and 20 Hz away from 1200, preferably approximately 1211 in one embodiment.

In another aspect of the invention, dark signals, or ambient light, are measured both before and after each of the light emitter wavelengths (red and infrared in one embodiment). Instead of simply subtracting one of the dark levels, the two dark levels are averaged and then subtracted from the detected signal. This compensates for a variation in ambient light during the detected signal, reducing the effect of power line interference or any other low frequency interference.

In a another aspect of the present invention, digital filtering and decimation are done in the digital domain. When there is a change in a gain setting on the front end hardware, or in the LED power, the filters are preloaded to put values in their memory to correspond to an estimate of the settled value of the output at the new gain or power settings. This preloading speeds up when valid data will be available at the output of the filter.

DETAILED DESCRIPTION OF THE INVENTION

Overall System

Figure 1:
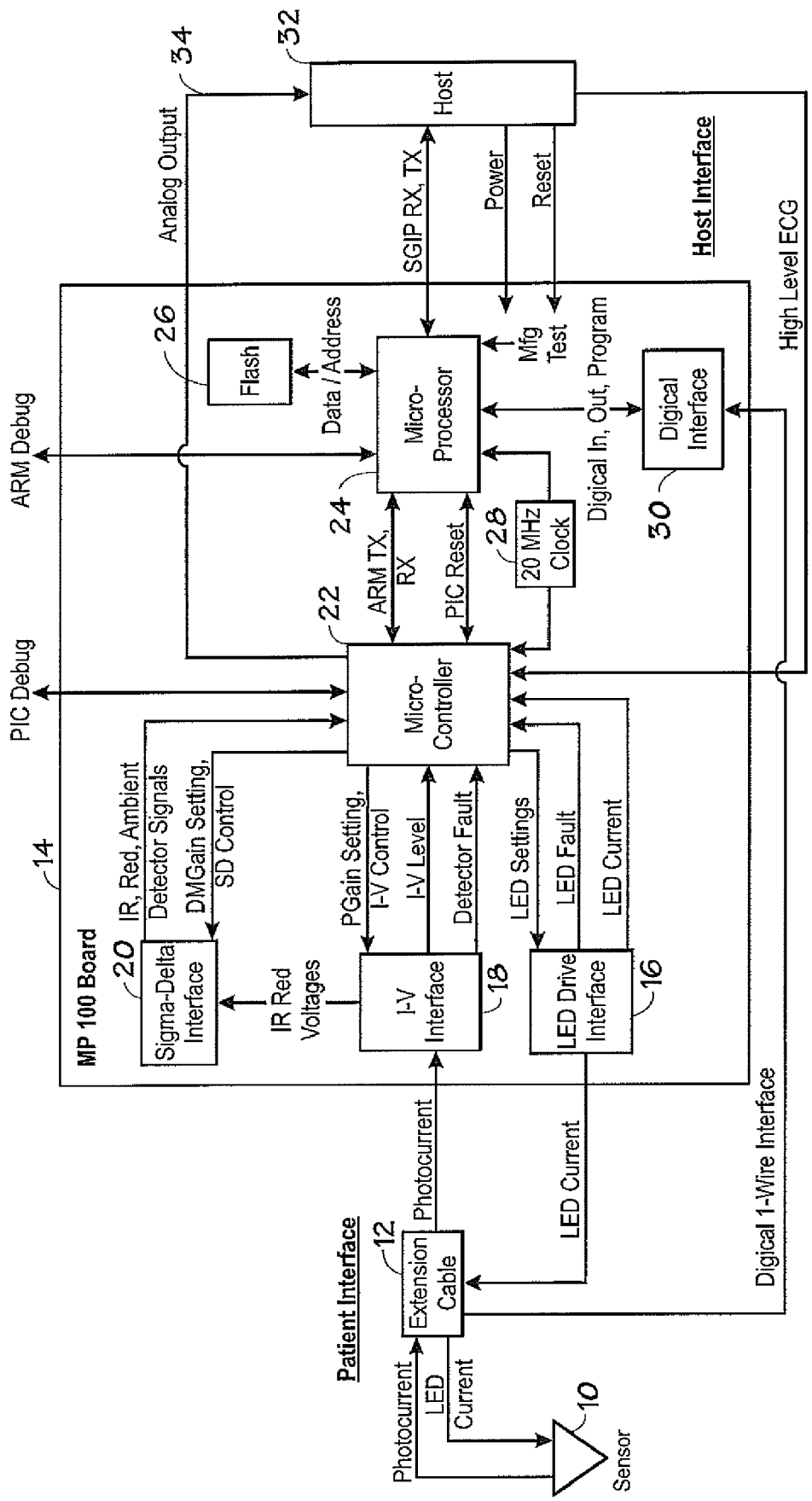
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22. Microcontroller 22 includes flash memory for a program, and EEPROM memory for data. The oximeter also includes a microprocessor chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Notch Filter

Figure 2:
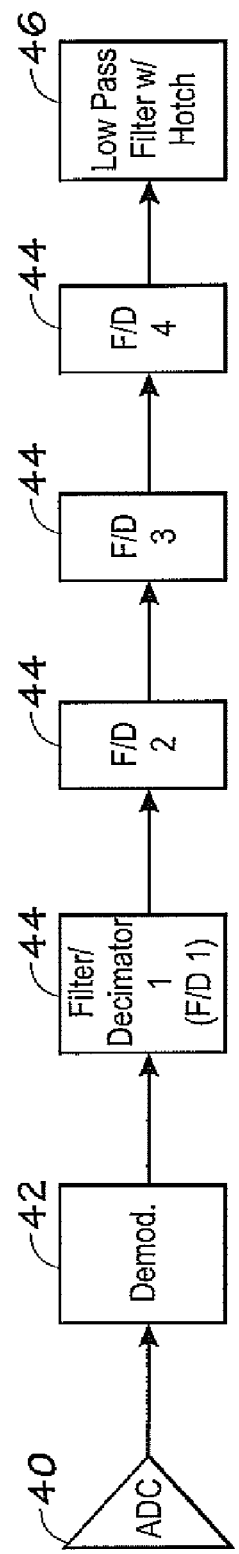
FIG. 2 is a block diagram of a portion of the digital manipulations in one embodiment of the invention, including a notch filter.

FIG. 2 shows an analog-to-digital converter 40 which provides a digital signal to be manipulated by microcontroller 22 of FIG. 1. The microprocessor would include a demodulator 42, four stages of filter/decimators 44, a low pass filter with a notch 46, as well as other blocks for digital manipulation of the signals and calculation of oxygen saturation as is well known in the art. Only the red channel is shown after the demodulation, but a similar channel is used for the IR signal.

Notch filter 46 deals with power line interference which, in the United States, comes from lights which operate on 60 Hz or 120 Hz, depending upon the power requirements. Europe and other areas use 50 Hz and 100 Hz. A common multiple of 50, 60, 100, and 120 Hz is 1200 Hz. The modulation bandwidth is chosen to be higher than the highest possible human pulse rate, preferably higher than 5 Hz. At the same time, it is chosen to be lower than any harmonic of the power line interference signals. Twenty hertz is chosen as a desirable upper limit because a second harmonic of 2450 will alias in at 2025 Hz. In one embodiment, the modulation frequency chosen is 1211.23 Hz. This is 11.23 Hz distant from 1200 Hz. (within a range of 5-20 Hz). Accordingly, in a preferred embodiment, a zero is provided in the notch filter at 11.23 Hz. The low pass filter with notch (46), in one embodiment, is an 8 pole Bessel filter with a notch at 11.25 Hz.

The present invention thus provides an effective means of eliminating interference from power line interference, such as the ripple on fluorescent lights which can alias onto the detected signal. Although anti-aliasing filters have been provided in hardware before a demodulator, it is difficult to make these effective, and thus there will be some residual line interference in the detected signal to be dealt with in the digital domain.

Averaging Ambient Dark Levels to Reduce Low Frequency Interference

Figure 3:
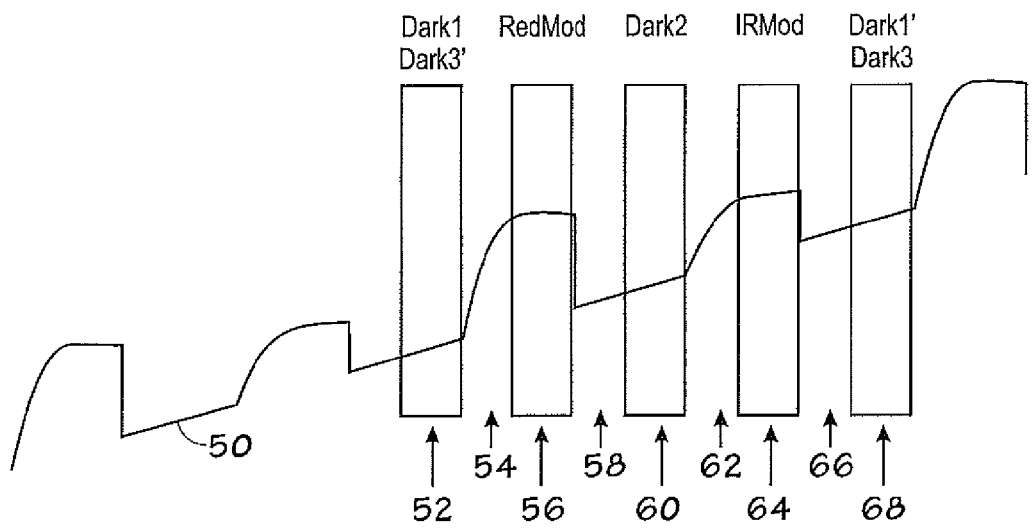
FIG. 3 is a diagram illustrating the multiple dark levels that are averaged in an embodiment of the invention.

FIG. 3 illustrates another aspect of the present invention, reducing ambient interference by averaging the ambient dark levels before and after a sampling period to account for low frequency interference from power lines or other sources. FIG. 3 shows a signal at a sampling rate of 2400. The upward sloping line in FIG. 3 is due to 60 Hz power line interference. It is desirable to eliminate the effect of this upward slope (which will be downward on other parts of the 60 Hz (or 50 Hz, etc.) signal.

FIG. 3 shows a detected signal during different periods of modulation. The detected signal level is illustrated by a line 50. During a first dark period 52, neither the red nor IR LED are on, allowing a sampling of the dark, or ambient, light. After this sampling, during a time period 54, the red LED is turned on, with signal 50 rising during this period as the red LED comes on to its full intensity. During the time period 56, the detected signal corresponds to the red LED being on.

After the red LED is turned off and the signal decays during a period 58, a second dark period 60 is sampled.

Subsequently, the IR LED is turned on during a period 62, and sampled during a period 64. It is turned off and the signal decays during a period 66, with a third dark sample being taken during a period 68. The third dark sample also corresponds to the first dark period 52, as the process repeats itself.

As can be seen from FIG. 3, if only one of the dark levels is used, an inaccurate ambient level may be measured if the ambient level is varying, such as due to a low frequency interference. By averaging the dark periods before and after the sampling period for a particular wavelength, a more accurate measurement of the ambient dark level signal is obtained. For example, the ambient interference during the red modulation period 56 is determined by measuring the dark 1 signal during period 52 and the dark 2 signal during period 60 and averaging these signals. Similarly, for the infrared modulation period 64, the dark 2 signal during period 60 and the dark 3 signal during period 68 are averaged and subtracted from the detected IR signal to eliminate the ambient interference. All of these calculations are done in the digital domain by microcontroller 22 of FIG. 1.

Preloading Decimation and Bessel Filters

Figure 4:
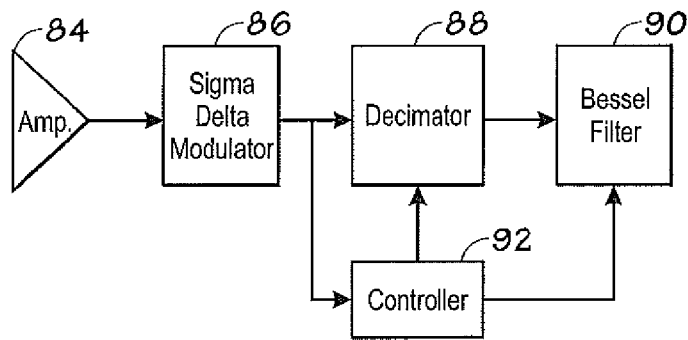
FIG. 4 is a diagram illustrating the preloading of the digital filter and decimator according to an embodiment of the present invention.

FIG. 4 illustrates another aspect of the present invention where filters and software are preloaded. Before the analog input signal is processed through the sigma-delta modulator and multi-bit analog digital converter, it is typically amplified in a hardware amplifier 84. After processing by the sigma-delta modulator 86 and conversion into digital domain, it is decimated to reduce the sample rate by a decimator 88 and filtered by a Bessel filter 88. A controller 92 pre-loads the memories of the Bessel filter and decimator with an estimate of what the settled value of the output would be. This will significantly reduce the settling time of the fitter after a step change in its input. Such a step change in the input can occur from a change in the gain settings of the amplifier 84. Alternately, a step change can be the result of a change in the particular LED being activated, the power of the LED, or other gain settings of the front end hardware. Since the controller 92 would be activating such changes, it will have the knowledge of when to pre-load the filter and decimator with the appropriate values. Although these are shown as blocks in FIG. 4, it is understood that in the preferred embodiment this is done by a software program which functions as controller 92, filter 88 and decimator 90. This preloading of the filter and decimator provides that valid data is available sooner by shortening the settling time.

As will be understood by those skilled in the art, the present invention may be embodied in other specific forms without departing from the essential characteristics thereof. For example, more than two different wavelengths of light could be used. Alternately, a different demodulation frequency could be chosen. In addition, the notch filtering can be done either before or after other digital processing of the detected signal. Accordingly, the foregoing description is intended to be illustrative, but not limiting, of the scope of the invention which is set forth in the following claims.

The invention claimed is:

1. A pulse oximetry system comprising:
    an emitter capable of directing one or more wavelengths of light into a tissue;
    a detector capable of detecting the one or more wavelengths of light to provide an analog sensor signal;
    an amplifier configured to amplify the analog sensor signal to provide an amplified analog sensor signal;
    a sigma-delta modulator having an input coupled to receive the amplified analog sensor signal;

a multiple bit analog-to-digital converter coupled to an output of the sigma-delta modulator to provide a digital signal;

a decimator configured to receive the digital signal and output a decimated signal;

a digital filter configured to operate on the decimated signal; and a controller configured to preload the decimator and digital filter with an estimate of a settled output value.

2. The pulse oximetry system, as set forth in claim 1, wherein the amplifier comprises a hardware amplifier.

3. The pulse oximetry system, as set forth in claim 1, wherein the digital filter comprises a Bessel filter.

4. The pulse oximetry system, as set forth in claim 1, wherein the controller comprises a control program.

5. The pulse oximetry system, as set forth in claim 1, wherein the controller is configured to preload the decimator and the digital filter after a step change in the decimated signal.

6. The pulse oximetry system, as set forth in claim 1, wherein the controller is configured to preload the decimator and the digital filter in response to a change in a gain setting of the amplifier.

7. The pulse oximetry system, as set forth in claim 1, wherein the controller is configured to preload the decimator and the digital filter in response to a change in an LED associated with the analog sensor signal being activated.

8. The pulse oximetry system, as set forth in claim 1, wherein the controller is configured to preload the decimator and the digital filter in response to a power change in an LED associated with the analog sensor signal.

9. The pulse oximetry system, as set forth in claim 1, wherein the controller is configured to preload the decimator and the digital filter in response to the controller changing a setting of the oximeter apparatus.

10. A non-transitory computer-readable medium, comprising executable instructions for:
controlling light at two wavelengths to be alternately driven into a tissue site using a modulation frequency that is a predetermined distance from a common multiple of 50, 60, 100, and 120, where the predetermined distance is greater than a highest pulse rate of a person and lower than a distance of any harmonic of 50, 60, 100, or 120;
processing a signal received from the tissue site to generate a processed signal;
notch filtering the processed signal at a frequency equivalent to the predetermined distance to produce a filtered signal; and
calculating at least one patient characteristic based on the filtered signal.

11. The non-transitory computer-readable medium, as set forth in claim 10 wherein processing the received signal comprises digitizing the received signal.

12. The non-transitory computer-readable medium, as set forth in claim 10 wherein the common multiple comprises 1200.

13. The non-transitory computer-readable medium, as set forth in claim 10 wherein the predetermined distance is between 5 and 20 hertz.

14. The non-transitory computer-readable medium, as set forth in claim 10 wherein the predetermined distance is approximately 11 hertz.

15. The non-transitory computer-readable medium, as set forth in claim 10 wherein the notch filtering is performed by providing a zero in a digital filter at the predetermined distance.

16. The non-transitory computer-readable medium, as set forth in claim 10 wherein calculating at least one patient characteristic comprises executable calculating a blood flow characteristic.

17. A non-transitory computer-readable medium for measuring a detected light signal in a pulse oximeter, comprising executable instructions for:
controlling light to be alternately driven into a tissue site using a modulation frequency to alternate between a first period of time when a first wavelength is being generated, a dark period of time when no light is being generated, and a second period of time when a second wavelength is being generated;
estimating a first level of ambient light in a signal received from the tissue site during the first period of time by averaging detected light received during the dark periods before and after the first period;
estimating a second level of ambient light in the signal received from the tissue site during the second period of time by averaging detected light received during the dark periods before and after the second period;
calculating a total light signal by subtracting the first level of ambient light from the signal received from the tissue site generated during the first period of time and subtracting the second level of ambient light from the signal received from the tissue site generated during the second period of time; and
calculating at least one patient characteristic based on the total light signal.

18. The non-transitory computer-readable medium, as set forth in claim 17 wherein calculating at least one patient characteristic comprises calculating a blood flow characteristic.

19. The non-transitory computer-readable medium, as set forth in claim 17 wherein calculating at least one patient characteristic comprises calculating an oxygen saturation.

20. The non-transitory computer-readable medium, as set forth in claim 17 wherein calculating at least one patient characteristic comprises calculating a pulse rate.

* * * * *